(12) United States Patent
Zajaczkowski et al.

(10) Patent No.: US 6,239,228 B1
(45) Date of Patent: May 29, 2001

(54) PRESSURE SENSITIVE ADHESIVE CONTAINING MACROMER HAVING REPEAT HYDROPHILIC MOIETIES

(75) Inventors: Michael J. Zajaczkowski, York; Barbara A. Stutzman, Dover, both of PA (US)

(73) Assignee: Adhesives Research, Inc., Glen Rock, PA (US)

( * ) Notice: Subject to any disclaimer, the term of this patent is extended or adjusted under 35 U.S.C. 154(b) by 0 days.

(21) Appl. No.: 09/471,236

(22) Filed: Dec. 23, 1999

Related U.S. Application Data

(63) Continuation of application No. 08/805,042, filed on Feb. 21, 1997, now abandoned.

(51) Int. Cl.$^7$ .................... C08F 265/04; C08F 267/06
(52) U.S. Cl. ............. 525/302; 525/296; 525/308
(58) Field of Search .................. 525/302, 296, 525/308

(56) References Cited

U.S. PATENT DOCUMENTS

| | | |
|---|---|---|
| 3,786,116 | 1/1974 | Milkovich et al. . |
| 3,832,423 | 8/1974 | Milkovich et al. . |
| 3,842,146 | 10/1974 | Milkovich et al. . |
| 3,862,077 | 1/1975 | Schulz et al. . |
| 3,879,494 | 4/1975 | Milkovich et al. . |
| 3,928,255 | 12/1975 | Milkovich et al. . |
| 3,989,768 | 11/1976 | Milkovich et al. . |
| 4,085,168 | 4/1978 | Milkovich et al. . |
| 4,551,388 | 11/1985 | Schlademan . |
| 4,554,324 | 11/1985 | Husman et al. . |
| 4,656,213 | 4/1987 | Schlademan . |
| 4,693,776 | 9/1987 | Krampe et al. . |
| 4,732,808 | 3/1988 | Krampe et al. . |
| 4,871,812 | 10/1989 | Lucast et al. . |
| 5,242,951 | 9/1993 | Akemi et al. . |
| 5,352,516 | 10/1994 | Therriault et al. . |
| 5,573,778 | 11/1996 | Therriault et al. . |
| 5,951,999 * | 9/1999 | Therriault et al. .......... 424/448 |

FOREIGN PATENT DOCUMENTS

| | | |
|---|---|---|
| 728780 | 8/1996 | (EP) . |
| 9514746 | 6/1995 | (WO) . |

* cited by examiner

*Primary Examiner*—James J. Seidleck
*Assistant Examiner*—Olga Asinovsky
(74) *Attorney, Agent, or Firm*—Birch, Stewart, Kolasch & Birch, LLP

(57) ABSTRACT

A graft copolymer pressure sensitive adhesive is provided comprised of a backbone polymer having a polymeric moiety grafted thereto. The copolymer comprises at least one A monomer consisting of a monomeric (meth)acrylic acid ester of a non-tertiary alcohol, optionally at least one B monomer, optionally at least one polymeric graft moiety C having a $T_g$ greater than 20° C., and a macromeric graft moiety D containing repeat hydrophilic units.

29 Claims, No Drawings

PRESSURE SENSITIVE ADHESIVE CONTAINING MACROMER HAVING REPEAT HYDROPHILIC MOIETIES

CROSS-REFERENCE TO RELATED APPLICATION

This application is a continuation application of application Ser. No. 08/805,042, filed Feb. 21, 1997, now abandoned.

BACKGROUND OF THE PRESENT INVENTION

The present invention is directed to a pressure sensitive adhesive containing hydrophilic components.

The transdermal delivery of therapeutic agents has been the subject of intense research and development for over 20 years. These efforts have resulted in the creation of several commercially successful products whose advantages over other dosage forms are well documented.

The skin, however, is an exceptionally well designed barrier. As a result, only a relatively small number of drug molecules are suitable for transdermal delivery.

Various techniques have been explored in an attempt to enhance the permeation of compounds which are not otherwise suitable for transdermal delivery. The most promising approaches have been found to be iontophoresis, electroporation, sonophoresis, and chemical enhancement. Of these methods, chemical enhancement is the more established, and is currently commercially employed.

Chemical enhancers, or percutaneous penetration enhancers, have a broad spectrum of chemical structure depending on the application in which they are to be employed. The most common enhancers belong to the following groups: non-ionic surfactants, alcohols, fatty acid esters, and amines.

In order for enhancers to function properly, they must be present at the skin/device interface in sufficiently high quantity (generally 5–40% percent by weight based on the weight of the adhesive). As most transdermal drug delivery devices utilize pressure sensitive adhesives as a means of providing intimate contact between the drug delivery means and the skin, it is essential that the adhesive polymer be compatible with the specific enhancer used. In this way, adequate concentrations of the enhancer can be achieved by proper formulation with the adhesive without disrupting the physical integrity of the adhesive.

Polyacrylates are well suited to obtain the desired compatibility in that the polarity of the pendant moieties can be altered to accommodate the structure of the enhancer. Unfortunately, it is generally observed that when enhancers are compounded with these adhesives, the compatibility may be too great, resulting in dramatic reduction in the cohesive strength of the adhesive system.

To reduce the loss of adhesive integrity, attempts have been made to crosslink the adhesive polymers. Although this does increase the cohesive strength, the adhesive often does not possess sufficient flow to allow for long term adhesion to skin.

Clearly, a proper balance of enhancer compatibility, cohesive strength, and polymer flow is required for properly designed adhesive/enhancer systems, especially in view of the fact that enhancers may either be oily or water-soluble materials which each present different compatibility problems.

Polymeric compositions are known which are comprised of backbone polymers having grafted thereto pendant polymeric moieties. The type of backbone polymer and graft polymeric moiety employed varies depending upon the desired characteristics of the end product. See, for example, U.S. Pat. Nos. 3,786,116; 3,832,423; 3,842,146; 3,862,077; 3,879,494; 3,928,255; 3,989,768; 4,085,168; 4,551,388; 4,554,324; 4,656,213; 4,693,776; 4,732,808; 4,871,812; and 5,352,516. These patents disclose various types of such polymers which may or may not exhibit pressure sensitive adhesive properties.

Typical of the type of polymeric compositions disclosed in the above patents are compositions comprised of a backbone polymer such as an acrylic or methacrylic backbone polymer having attached thereto a graft polymer comprised of a polymerizable macromolecular monomer such as styrene or alpha-methylstyrene. See, for example, U.S. Pat. No. 4,554,324, and commonly-assigned U.S. Pat. No. 5,352,516, among others, in this regard.

The acrylic pressure sensitive adhesives such as described in U.S. Pat. No. 4,554,324 and U.S. Pat. No. 5,352,516 may be made from an acrylic ester and a polar acrylic monomer. The polar acrylic monomer can be one or a mixture of acrylic acid, acrylamide, acrylonitrile, itaconic acid, etc. The acrylic ester can be any aliphatic ester of acrylic acid. Such monomers are typically polymerized free radically by solution, suspension or emulsion polymerization. The acrylate portion of the copolymer is generally present in a generally high concentration and renders the polymer tacky. The polar monomer increases the ability of the adhesive to bond to a surface.

U.S. Pat. Nos. 4,693,776 and 4,732,808 also disclose a pressure sensitive skin adhesive composition comprised of a macromer-reinforced acrylate copolymer. U.S. Pat. No. 4,871,812 discloses a moldable medical adhesive comprising a blend of an acrylate terpolymer adhesive containing a hydrophilic macromer moiety, and a reinforcing material which is a carbonylamido group containing polymer. U.S. Pat. No. 4,656,213 is directed to an acrylic hot melt pressure sensitive adhesive comprising a polyacrylate graft copolymer which may be plasticized to enhance the adhesive properties thereof.

Such adhesives have been found to suffer from the disadvantage that their adhesive properties are not sufficiently compatible with the skin (due to inadequate long-term tack) with the result that adhesive failure may occur after a short time due to movement of the skin.

It has accordingly been found that reinforcement of the adhesive through the use of graft polymeric moieties or macromers, followed by plasticization with conventional percutaneous penetration enhancers, allows for the desired level of cohesiveness while allowing for a degree of adhesive flow which is essential for long term adhesion to skin.

However, it is still desirable to provide a transdermal adhesive which may be used with either an oily or water-soluble drug flux or skin permeation enhancer or mixtures of same. This avoids the need to use separate adhesive formulations depending upon whether the enhancer is oil or water-soluble.

OBJECTS AND SUMMARY OF THE PRESENT INVENTION

It is accordingly an object of the present invention to provide a pressure sensitive adhesive which exhibits hydrophilic properties.

It is also another object of the present invention to provide a pressure sensitive adhesive which possesses adequate compatibility with both oily and water-soluble percutaneous penetration enhancers and which may accordingly be used with advantage in a transdermal drug delivery device.

In accordance with the present invention, there is thus provided a graft copolymer pressure sensitive adhesive comprised of a backbone polymer having a polymeric moiety grafted thereto, said graft copolymer comprising the reaction product of:

(1) at least one A monomer consisting of a monomeric acrylic or methacrylic acid ester of a non-tertiary alcohol, said alcohol having from 1 to 30 carbon atoms, wherein at least about 30 percent by weight of said A monomer consists of a monomeric acrylic or methacrylic acid ester of a non-tertiary alcohol having at least 12 carbon atoms, and said at least one A monomer exhibiting an average number of carbon atoms in the alcohol portion of the total acrylic or methacrylic acid esters of at least 10, (2) optionally at least one B monomer, (3) optionally at least one polymeric graft moiety C having a $T_g$ greater than 20° C., and (4) a polymeric graft moiety D containing repeat hydrophilic units, preferably a polyether or polyester-based graft moiety.

DETAILED DESCRIPTION OF THE INVENTION

The present invention is a graft copolymer pressure sensitive adhesive comprised of a backbone polymer having a polymeric moiety grafted thereto. The graft copolymer comprises the reaction product of at least one A monomer (as defined), optionally at least one B monomer, optionally a polymeric graft moiety C having a $T_g$ greater than 20° C., and a polymeric graft moiety D containing repeat hydrophilic units.

The graft copolymer includes at least one A monomer consisting of a monomeric (meth)acrylic acid ester of a non-tertiary alcohol where the alcohol portion has from 1 to 30 carbon atoms. Exemplary A monomers include but are not limited to esters of acrylic acid or methacrylic acid with non-tertiary alcohols such as 1-butanol, 1-pentanol, 2-pentanol, 3-pentanol, 2-methyl-i-butanol, 1-methyl-1-pentanol, 2-methyl-l-pentanol, 3-methyl-l-pentanol, 2-ethyl-1-butanol, 3,5,5-trimethyl-1-hexanol, 3-heptanol, 2-octanol, 1-decanol, 1-dodecanol, etc.

Advantageously, it has been found useful to employ at least one A monomer formed from an alcohol having at least 12 carbon atoms. The use of an A monomer formed from an alcohol having at least 18 carbon atoms is particularly desirable. Such exemplary A monomers include but are not limited to lauryl acrylate ($C_{12}$), tridecylacrylate ($C_{13}$), myristyl acrylate ($C_{14}$), palmityl acrylate ($C_{16}$) and stearyl acrylate ($C_{18}$). Such monomers are well-known to those skilled in the art.

The presence of an A monomer having a carbon chain of at least 12 carbon atoms has been found to enhance the compatibility of the adhesive with oily or non-water soluble drug flux or skin permeation enhancers which are conventionally employed in transdermal drug delivery devices. Such enhancers have not been found to be particularly compatible with conventional transdermal adhesives containing a major portion of A monomers formed from alcohols having from 4 to 12 carbon atoms. While the use of A monomers formed from alcohols having from 4 to 12 carbon atoms in the adhesive of the present invention is appropriate, it is preferable for the at least one A monomer component to comprise at least 30 percent by weight of an A monomer formed from an alcohol having at least 12 carbon atoms. At least one A monomer component (if more than one A monomer is present) will exhibit an average number of carbon atoms in the alcohol portion of the total acrylic or (meth)acrylic acid esters of from 4 to 16, and preferably at least 10.

One or more optional polymerizable B monomers may be incorporated in the copolymer which B monomer(s) is copolymerizable with the A monomer. Such additional B monomer(s) may be either hydrophilic or hydrophobic.

Exemplary optional B monomers include vinyl monomers having at least one nitrogen atom. Such monomers (each of which exhibit a $T_g$ of >20° C.) include but are not limited to N-mono-substituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide, and N,N-dihydroxyethylacrylamide, etc.

Other optional B monomers may include, for example, various vinyl monomers such as acrylic and methacrylic acid, itaconic acid, crotonic acid, methoxyethyl acrylate or methacrylate, ethyoxyethyl acrylate or methacrylate, glycerol acrylate or methacrylate, hydroxyethyl methacrylate, hydroxypropyl methacrylate, beta-carboxyethyl acrylate, vinyl pyrrolidone and vinyl caprolactam (each of which also exhibit a $T_g$ of >20° C.). One or more B monomers may be employed.

The optional graft polymeric moiety C has a $T_g$ greater than 20° C. Graft polymeric moiety C has the formula X-Z wherein X is a group copolymerizable with monomers A and B or capable of attachment to copolymerized A and B monomers and Z is a polymeric graft moiety having a $T_g$ greater than 20° C. The Z moiety is essentially unreactive under copolymerization conditions.

More specifically, the X moiety is an unsaturated polymerizable moiety the composition of which is not critical. The X moiety may be, for example, when intended to be copolymerizable with monomers A and B, simply a vinyl group of the formula $CHR=CR^1$-where R is hydrogen or COOH and $R^1$ is hydrogen or alkyl such as methyl. Other exemplary X moieties include but are not limited to methacryloyl, maleoyl, itaconoyl, crotonoyl, unsaturated urethane moiety, methacrylamido and moieties of the formula $CH_2=CHCH_2O-$.

The X moiety may comprise an amine or alcohol moiety (such as a monohydroxyl or monoamine moiety) which permits attachment of the macromer to a suitable functionality on previously-polymerized monomers A and B. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A variety of functional groups may be employed to attach the graft Z to the polymer backbone.

Exemplary functional groups include but are not limited to

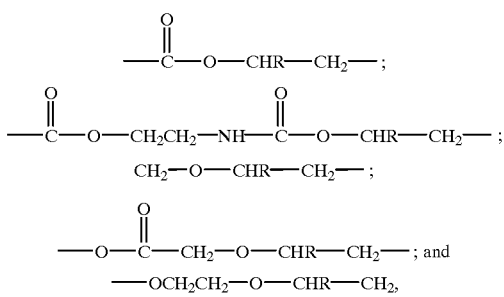

where R is a hydrogen atom or a lower alkyl group.

With regard to the optional polymeric graft moiety C portion of the adhesive composition, U.S. Pat. Nos. 3,786, 116; 3,842,057; 3,842,058; 3,842,059; 3,862,098; 3,862, 101, 3,862,102 and 4,554,324 disclose polymerizable macromers which are suitable for use as graft moieties on a backbone polymer as defined.

Preferably, the polymeric moiety C is formed from a vinyl aromatic monomer such as styrene, alpha-methylstyrene, indene and p-tert-butylstyrene. However, the polymeric moiety Z may also be formed from vinyl toluene, acenaphthalene, acrylonitrile and methacrylonitrile; organic isocyanates including lower alkyl, phenyl, lower alkyl phenyl and halophenyl isocyanates; organic diisocyanates including lower alkylene, phenylene, and tolylene diisocyanates; lower alkyl and allyl acrylates and methacrylates, including methyl, t-butyl acrylates, and methacrylates; lower olefins, such as ethylene, propylene, butylene, isobutylene, pentene, hexene, etc.; vinyl esters of aliphatic carboxylic acids such as vinyl acetate, vinyl propionate, vinyl octoate, vinyl oleate, vinyl stearate, vinyl benzoate, vinyl lower alkyl ethers; conjugated dienes such as isoprene and butadiene; 2-oxazolines such as 2-ethyl-2-oxazoline; and vinyl unsaturated amides such as acrylamide, methylacrylamide, N,N-di(lower alkyl) acrylamides such as N,N-dimethylacrylamide.

The selection of the specific polymerizable monomer for the polymer graft is not critical, since as the above listing suggests, a wide variety of monomers (and the resulting polymeric moieties) can be used with success as a polymeric graft in the claimed composition which meet the minimum $T_g$ requirement.

The molecular weight of the graft polymeric moiety C is preferably sufficient to result in the formation of a "phase-separated" graft copolymer composition. Generally the molecular weight of the graft polymeric moiety will be within the range of from about 2,000 to 60,000, and will preferably range from about 2,000 to 13,000.

The graft polymeric moiety D also forms polymeric sidechains on the copolymer. The macromer D contains repeat hydrophilic units.

The macromer D may be represented by the formula X-(Y)$_p$-Z-R. X is as defined above and is a moiety copolymerizable with monomers A and B or, in the alternative, capable of attachment to polymerized monomers A and B, Y is a divalent linking group, Z is a homo- or copolymeric moiety essentially unreactive at copolymerization conditions containing repeat hydrophilic units, R is a terminal group, and p is 0 or 1.

A preferred Y divalent linking group is

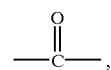

or a linking group which incorporates such a moiety.

Additional Y linking groups which may be employed in connection with the present invention include but are not limited to the following moieties:

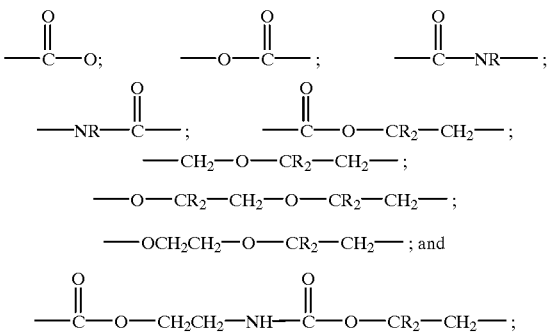

where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842, 058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyester(meth)acrylate radical, polyvinyl caprolactam radical, polymethylvinyl ether radical or mixtures thereof. Exemplary D macromers formed from such radicals include but are not limited to ethoxylated or propoxylated hydroxy(Cl.$_5$)alkyl meth(acrylate), polymethylvinyl ether mono(meth)acrylate and beta-carboxyethyl acrylate. The molecular weight of the macromer used in the present invention is not critical but will generally range from about 300 to about 50,000, and preferably from about 300 to 3,000.

The Z moiety is preferably comprised solely of one or more hydrophilic monomer radicals. However, the Z moiety may also be a copolymer of hydrophilic and hydrophobic monomers. Desirably, any non-hydrophilic portion employed in the D macromer is present in an amount of 50% or less based on the weight of the macromer.

The macromer D is preferably represented by the formula:

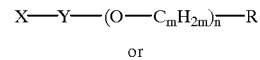

or

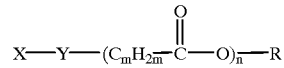

wherein X and Y are as defined above and R represents a terminal group; and in which m is an integer of from 2 to 6, and n ranges up to 300.

More specifically, macromer D may be an ethoxylated or propoxylated hydroxy($C_{1-5}$)alkyl (meth)acrylate represented by the formula:

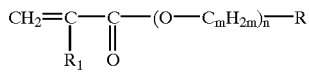

wherein $R_1$ is hydrogen or $C_{1-5}$ alkyl and R is a terminal group. Preferably, m is 2 or 3 and n is 5 to 30, and R is H, OH, $C_{1-5}$ alkyl, or nonyl-phenol.

Alternatively, macromer D may advantageously comprise a 2-carboxy($C_{1-5}$)alkyl acrylate of the formula:

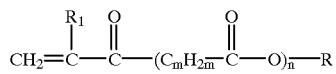

where $R_1$ is hydrogen or $C_{1-5}$ alkyl and R is a terminal group. Preferably, m is 2 or 3 and n is 4 to 30, and R is H, OH, $C_{1-5}$ alkyl or nonyl-phenol.

Of course, macromer D may incorporate mixtures of polyether and polyester repeat units with advantage in a variety of ratios. Such ratios are non-critical to practice of the present invention.

The macromer D may employ a variety of terminal groups R. While the terminal group may typically be OH or $C_{1-5}$ alkyl, it may be desirable to select a terminal group based on the functional character of the terminal group. For instance, suitable terminal groups include but are not limited to (1) acid/ionic groups such as carboxyl, phosphate or sulfate groups, (2) hydrophobic groups such as lower alkyl, phenyl or substituted phenyl, and (3) hydrophilic groups such as hydroxyl or amine groups.

Depending upon the terminal group employed, ionic end groups may be used to provide pH-dependent solubility characteristics for the copolymer. Hydrophobic terminal groups may be used to reduce the water sensitivity of the copolymer.

Other physical properties or characteristics of the copolymer may be modified by selection of suitable terminal groups. The copolymer of the present invention may be covalently or ionically-crosslinked in a conventional manner. Ionic terminal groups may be used to provide a desired degree of crosslinking; for example, by neutralizing acid moieties with metal hydroxides. High temperature performance may be enhanced by incorporating an acid functionality in conjunction with a ditertiary amine. Aqueous solution viscosities may be influenced by the presence of ionic terminal groups.

Preferably, the A monomer is present in the graft copolymer in an amount of from 20 to 80 percent by weight, the optional B monomer is present in an amount of from 3 to 30 percent by weight, the optional C macromer is present in an amount of from 2 to 15 percent by weight, and the D macromer is present in an amount of from 5 to 60 percent by weight, based on the total weight of the respective components A, B, C and D in the graft copolymer.

It may be advantageous to incorporate a tackifier or plasticizer into the copolymer to enhance tack. Exemplary tackifiers include but are not limited to polyethylene glycol, polypropylene glycol, and suitable polyoxyethylene-based compounds. Suitable polyoxyethylene-based tackifiers are disclosed at column 6 of U.S. Pat. No. 4,413,080, herein incorporated by reference in its entirety. Other suitable tackifiers include conventional hydrogenated rosin ester compounds. Polyalicyclic tackifiers include those based on aromatic copolymers of styrene, alpha-methyl styrene and indene followed by hydrogenation. Such tackifiers, if present, may be employed in an amount of up to about 50 percent by weight, based on the total weight of the composition. Plasticizers may be used in amounts of up to about 20% by wt. Exemplary plasticizers include but are not limited to adipate and glutarate esters, hydrogenated rosin esters and reduced alcohol derivatives, as well as hydrogenated poly(aromatic) copolymers and mineral or paraffin oils. Preferred plasticizers include citric acid esters such as those marketed under the name Citrof lex which include triethyl citrate, acetyltriethyl citrate, tri-n-butyl citrate, acetyltri-n-butyl citrate.

As noted above, the copolymer composition of the present invention may be prepared by any conventional polymerization technique, including (1) free radical-initiated copolymerization of components A and D and optionally B and C in the presence of a solvent, or (2) attachment of the macromer grafts to a preformed backbone polymer formed from copolymerized monomer A optionally copolymerized with monomer B via reaction with a suitable functional group on the backbone polymer subsequent to formation of same.

Suitable copolymerization temperatures range from about 20° C. to about 150° C. for periods of time of from 2 to 24 hours until the desired degree of conversion occurs. Upon completion of the copolymerization process, the solvent is removed and a tacky copolymer results having acceptable adhesive properties. If desired, a suitable crosslinking agent may be employed to increase the molecular weight of the adhesive if desired.

The adhesive of the present invention may be used in association with a variety of body members (e.g., tapes, patches, strips, labels, etc.) to provide an adhesive assembly. For example, the body member may be in the form of a backing material coated on at least one side thereof with the adhesive to provide an adhesive-backed sheet film or tape. Exemplary backing materials used in the production of such a product include but are not limited to flexible and inflexible backing materials conventionally employed in the area of pressure sensitive adhesives, such as creped paper, kraft paper, fabrics (knits, non-wovens, wovens), foil and synthetic polymer films such as polyethylene, polypropylene, polyvinyl chloride, poly(ethylene terephthalate) and cellulose acetate, as well as glass, ceramics, metallized polymer films and other compatible sheet or tape materials.

The body member (e.g., in sheet form) may be coated in any conventional manner with the adhesive composition of the present invention, such as by roll coating, spray coating, extrusion coating, co-extrusion coating, hot melt coating by use of conventional coating devices. When appropriate, the adhesive of the present invention may be applied as a solution to at least one surface of the body member and the solvent subsequently removed to leave a tacky adhesive residue on the body member. The adhesive may be applied to the body member either in the form of a continuous layer or in discontinuous form.

The adhesive may be used with particular advantage as a transdermal adhesive in association with a percutaneous penetration enhancer in a transdermal drug delivery device. Percutaneous penetration enhancers have the ability to increase permeability of skin to transdermally-administered pharmacologically active agents. Such enhancers are well-known in the art, and are discussed at length in U.S. Pat. Nos. 5,059,426 and 5,175,052, each herein incorporated by reference. By way of brief summary, such enhancers include but are not limited to surfactants (anionic, nonionic, cationic, zwitterionic), lipophilic solvents (terpenes, lactams), hydrophilic solvents (polyols, fatty acid esters, alcohols, sulfoxides), etc. Preferably, such enhancers are selected from the group consisting of sorbitols, ethoxylated alkyl phenols, gycerol, propylene glycol, polyethylene glycols, fatty acid esters, alcohols, and amines, and may be either water-soluble or non-water-soluble (i.e., oily).

It has been found that the pressure sensitive adhesive of the present invention can be used with advantage upon admixture of percutaneous penetration enhancers with the base polymer to form a drug flux enhancer-tolerant pressure sensitive adhesive composition. That is, both oily or water-soluble percutaneous penetration enhancers can be admixed with the base polymer to maximize the ability of an incorporated pharmacologically active agent to be absorbed into the skin without adversely affecting the adhesive properties of the adhesive. Advantageously, it has been found that the percutaneous penetration enhancer can be used in amounts up to about 40 percent by weight, based on the weight of the composition, without adversely affecting the physical integrity of the adhesive or its adhesive properties. Such advantages can be attained irrespective of whether the percutaneous penetration enhancer is either oil or water-soluble which result is not well-attained by conventional adhesives. Preferably, the enhancer will be employed in an amount within the range of from 5 to 30 percent by weight, based on the weight of the composition.

The adhesive of the present invention may be used with advantage in a variety of conventional transdermal drug delivery devices. Such devices may take many forms. Generally, such devices comprise a backing material and an adhesive layer on at least a portion of the backing material. A release liner covers the adhesive layer until use at which time the liner is removed and the adhesive layer placed on the skin. The backing material is impermeable to the pharmacologically active agent. The pharmacologically active agent may be contained in either a liquid reservoir within the backing layer, within a matrix layer on said backing layer disposed between the adhesive layer and the backing layer, or within a layer of the drug flux enhancer-adhesive composition of the present invention. The manner of formulation of such various transdermal drug delivery systems is within the ability of one skilled in the art.

EXAMPLE 1

A reaction mixture was prepared and 0.11 wt. % BPO was used as the catalyst. 30% of the mixture was charged to a 1-liter reaction vessel. Under a nitrogen atmosphere, the batch was heated to 72° C. over 15 minutes. After the initial 15 minutes, the remaining 70% of monomer/solvent mixture was added over 4 hours, maintaining a batch temperature of 71.5–74° C. Upon completion of the addition, the reactants were polymerized for 1 additional hour to produce a tackifier-free pressure sensitive adhesive. The reactor feed mix consisted of the following components:

| Monomers | Amount |
|---|---|
| Polystyrene methacrylate (macromer C) | 21.00 grams |
| Ethoxylated nonyl-phenol acrylate (macromer D) | 25.84 |
| Isooctyl acrylate (A monomer) | 56.52 |
| Hydroxy ethyl acrylate (B monomer) | 64.60 |
| Isobornyl acrylate (A monomer) | 25.84 |
| Lauryl acrylate (A monomer) | 96.90 |

| | -continued |
|---|---|
| Stearyl acrylate (A monomer) | 32.30 |
| Solvents | Amount (Grams) |
| Ethyl acetate | 474.30 grams |
| Toluene | 52.70 |

EXAMPLE 2

The procedure of Example 1 was repeated using the following reactor feed components to produce a tackifier-free pressure sensitive adhesive with the exception that the reactants were added over 3.5 hours with a subsequent 1.5 hour reaction time:

| | Amount |
|---|---|
| Monomers | |
| Polystyrene methacrylate (macromer C) | 23.20 grams |
| Ethoxylated nonyl-phenol acrylate (macromer D) | 83.90 |
| Hydroxyl ethyl acrylate (B monomer) | 71.40 |
| Lauryl acrylate (A monomer) | 133.88 |
| Stearyl acrylate (A monomer) | 44.62 |
| Solvents | |
| Ethyl acetate | 330.31 grams |
| Toluene | 147.90 |
| Isopropyl alcohol | 14.79 |

EXAMPLE 3

The procedure of Example 1 was repeated using the following reactor feed components to produce a tackifier-free pressure sensitive adhesive with the exception that the reactants were added over 3.5 hours with a subsequent 1.5 hour reaction time:

| Monomers | Amount (wt. %) |
|---|---|
| Polystyrene methacrylate (macromer C) | 23.21 grams |
| Ethoxylated nonyl-phenol acrylate (macromer D) | 71.40 |
| Hydroxyl ethyl acrylate (B monomer) | 85.68 |
| Lauryl acrylate (A monomer) | 107.09 |
| Stearyl acrylate (A monomer) | 33.92 |
| Isobornyl acrylate (A monomer) | 35.70 |
| Solvents | Amount |
| Ethyl acetate | 330.31 grams |
| Toluene | 147.90 |
| Isopropyl alcohol | 14.79 |

EXAMPLE 4

The procedure of Example 1 was repeated using the following reactor feed components to produce a tackifier-free pressure sensitive adhesive, with the exception that the reactants were added over 3.5 hours with a subsequent 1.5 hour reaction time:

|  | Amount |
| --- | --- |
| Monomers | |
| Tridecyl acrylate (A monomer) | 178.50 grams |
| Ethoxylated nonyl-phenol acrylate (macromer D) | 76.76 |
| Hydroxyl ethyl acrylate (B monomer) | 71.40 |
| Polystyrene methacrylate (macromer C) | 30.34 |
| Solvents | |
| Ethyl acetate | 330.31 grams |
| Isopropyl alcohol | 14.79 |
| Toluene | 147.90 |

EXAMPLE 5

The procedure of Example 1 was repeated using the following reactor feed components to produce a tackifier-free pressure sensitive adhesive, with the exception that the reactants were added over 3 hours with a subsequent 1 hour reaction time:

|  | Amount |
| --- | --- |
| Monomers | |
| Isooctyl acrylate (A monomer) | 144.00 grams |
| Ethoxylated nonyl-phenol acrylate (D macromer) | 144.00 |
| Beta-carboxyethyl acrylate (D macromer) (n = 4–6) | 16.20 |
| Beta-carboxyethyl acrylate (B monomer) (n = 2–3) | 37.80 |
| Polystyrene methacrylate (C macromer) | 18.00 |
| Solvents | |
| Ethyl acetate | 352.00 grams |
| Isopropyl alcohol | 22.00 |
| Toluene | 66.00 |

EXAMPLE 6

The procedure of Example 5 was repeated with the exception that the following components were added to the completed polymer product of Example 5 to yield a crosslinked adhesive:

Foral 105 rosin tackifier (50% solution)
Citroflex B-6 citric acid ester plasticizer (20% solution)
Xama-7 aziridine crosslinker (0.75%)

EXAMPLE 7

The procedure of Example 3 was repeated using the following reaction feed components to produce a tackifier-free pressure sensitive adhesive:

|  | Amount |
| --- | --- |
| Monomers | |
| Isooctyl acrylate (A monomer) | 72.00 grams |
| Tridecyl acrylate (A monomer) | 72.00 |
| Ethoxylated nonyl-phenol acrylate (D macromer) | 144.00 |
| Beta-carboxyethyl acrylate (D macromer) (n = 4–6) | 16.20 |
| Beta-carboxyethyl acrylate (B monomer) (n = 2–3) | 37.80 |
| Polystyrene methacrylate (C macromer) | 18.00 |
| Solvents | |
| Ethyl acetate | 352.00 grams |
| Isopropyl alcohol | 22.00 |
| Toluene | 66.00 |

What is claimed is:

1. A normally tacky copolymer having pressure sensitive adhesive properties comprised of a backbone polymer having at least one polymeric moiety grafted thereto, comprising the reaction product of:

(1) at least one A monomer comprising a monomer acrylic or methacrylic acid aliphatic ester of a non-tertiary monoalcohol, said alcohol having from 1 to 30 carbon atoms, wherein at least about 30 percent by weight of said A monomer comprises a monomeric acrylic or methacrylic acid aliphatic ester of a non-tertiary alcohol having at least 12 carbon atoms, and said at least one A monomer exhibiting an average number of carbon atoms of at least 10 in the alcohol portion of the total acrylic or methacrylic acid aliphatic esters of non-tertiary monoalcohols, (2) optionally at least one B monomer, said backbone polymer formed from said A and B monomers, (3) optionally an polymeric graft moiety C having a $T_g$ greater than 20° C., and (4) a graft macromer D containing repeat hydrophilic units, and wherein said A monomer is present in said copolymer in an amount within the range of from about 20 to 80 percent by weight.

2. The copolymer of claim 1 wherein a graft moiety C is present which is a polymerized monoalkenyl-substituted aromatic hydrocarbon.

3. The copolymer of claim 2 wherein said polymerized monoalkenyl-substituted aromatic hydrocarbon comprises polystyrene.

4. The copolymer of claim 1 wherein the molecular weight of said graft moiety C is in the range of from about 2,000 to 30,000.

5. The copolymer of claim 1 wherein said at least one A monomer comprises an ester of acrylic or methacrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

6. the copolymer of claim 1 wherein the B monomer is present in the copolymer in an amount within the range of from about 3 to 30 percent by weight.

7. The copolymer of claim 1 wherein the D macromer is present in the copolymer in an amount within the range of from about 5 to 60 percent by weight.

8. The copolymer of claim 1 wherein said B monomer has a $T_g$ of >20° C.

9. The copolymer of claim 1 wherein a B monomer is present selected from the group consisting of hydroxy($C_1$-

$_5$)alkyl acrylates, hydroxy($C_{1-5}$)alkyl methacrylates, dihydroxy($C_{1-5}$)alkyl acrylates, dihydroxy($C_{1-5}$)alkyl methacrylates and mixtures thereof.

10. The copolymer of claim 1 wherein a B monomer is present comprising a vinyl monomer having at least one nitrogen atom.

11. The copolymer of claim 10 wherein said B monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

12. The copolymer of claim 1 wherein said macromer D is defined by the formula X-(Y)$_p$-Z-R, wherein X is a moiety copolymerizable with monomers A and B or capable of attachment to copolymerized monomers A and B, Y is a divalent linking group, Z is a homo- or copolymeric moiety containing repeat hydrophilic units, R is a terminal group, and p is 0 or 1.

13. The copolymer of claim 12 wherein X is a (meth)acrylate moiety.

14. The copolymer of claim 1 wherein macromer D is a polyether or polyester (meth)acrylate moiety.

15. The copolymer of claim 12 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

16. The copolymer of claim 1 wherein said macromer D is defined by the formula:

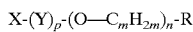

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

17. The copolymer of claim 16 wherein said macromer D is defined by the formula

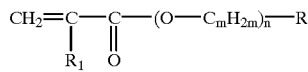

wherein $R_1$ is hydrogen or $C_{1-5}$ alkyl and R is a terminal group.

18. The copolymer of claim 17 wherein R is OH or $C_{1-5}$ alkyl.

19. The copolymer of claim 17 wherein n is an integer of from 5 to 30.

20. The copolymer of claim 1 wherein an A monomer is present comprising a monomeric acrylic or methacrylic acid aliphatic ester of a non-tertiary monoalcohol which has from 12 to 18 carbon atoms.

21. The copolymer of claim 1 wherein said macromer D is selected from the group consisting of ethoxylated hydroxy ($C_{1-5}$ alkyl) acrylate, propoxylated hydroxy ($C_{1-5}$ alkyl) acrylate, ethoxylated hydroxy ($C_{1-5}$ alkyl) methacrylate, and propoxylated ($C_{1-5}$ alkyl) methacrylate.

22. The copolymer of claim 1 wherein said macromer D is selected from the group consisting of ethoxylated and propoxylated hydroxy ($C_{1-5}$ alkyl) (meth)acrylate, poly(2-ethyl-2-oxazoline), polyacrylic acid, polyvinyl alcohol, polyvinyl pyrrolidone, polyvinyl caprolactam and polymethylvinyl ether mono (meth) acrylate.

23. The copolymer of claim 1 wherein said macromer D is 2-carboxy($C_{1-5}$)alkyl acrylate.

24. The copolymer of claim 1 wherein said macromer D is defined by the formula:

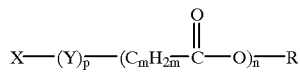

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

25. The copolymer of claim 24 wherein R is OH or $C_{1-5}$ alkyl.

26. The copolymer of claim 24 wherein n is an integer of from 4 to 30.

27. The copolymer of claim 1 which is crosslinked.

28. The copolymer of claim 16 which is crosslinked.

29. The copolymer of claim 24 which is crosslinked.

* * * * *